(12) United States Patent
Dos Santos

(10) Patent No.: US 9,333,115 B2
(45) Date of Patent: May 10, 2016

(54) SEPARATION OF GAS AND LIQUID IN MEMBRANE VALVES

(71) Applicant: Alcon Research, Ltd., Fort Worth, TX (US)

(72) Inventor: Cesario P. Dos Santos, Aliso Viejo, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 389 days.

(21) Appl. No.: 13/710,016

(22) Filed: Dec. 10, 2012

(65) Prior Publication Data

US 2013/0150778 A1   Jun. 13, 2013

Related U.S. Application Data

(60) Provisional application No. 61/569,984, filed on Dec. 13, 2011.

(51) Int. Cl.
*A61F 9/007* (2006.01)
*B65D 27/32* (2006.01)
*A61M 39/24* (2006.01)

(52) U.S. Cl.
CPC .... *A61F 9/00781* (2013.01); *A61M 2039/2433* (2013.01)

(58) Field of Classification Search
CPC ...... A61F 9/00781; A61F 9/007; B65D 27/32
USPC ............................................................ 604/8, 9
See application file for complete search history.

(56) References Cited

U.S. PATENT DOCUMENTS

| 6,881,197 | B1* | 4/2005 | Nigam | A61F 9/00781 |
| | | | | 604/8 |
| 2004/0010219 | A1* | 1/2004 | McCusker | A61M 27/006 |
| | | | | 604/9 |
| 2006/0052768 | A1* | 3/2006 | Joshi | A61K 9/0004 |
| | | | | 604/892.1 |
| 2009/0306594 | A1* | 12/2009 | Pang et al. | 604/133 |
| 2010/0331858 | A1* | 12/2010 | Simaan | A61F 2/82 |
| | | | | 606/130 |
| 2011/0071458 | A1* | 3/2011 | Rickard | 604/9 |

* cited by examiner

*Primary Examiner* — Philip R Wiest
*Assistant Examiner* — Sara Sass
(74) *Attorney, Agent, or Firm* — Haynes and Boone, LLP

(57) ABSTRACT

A drainage device for implantation in an eye of a patient to treat an ocular condition is disclosed. The drainage device includes a housing, a multi-compartment flow control chamber, and a membrane. The housing includes an entrance port and an exit port connected by a fluid flow passageway. The membrane is disposed between the fluid flow passageway and the multi-compartment flow control chamber, which includes a first compartment and a second compartment in fluid communication with each other. The first and second compartments are structurally arranged to limit contact of gas with the membrane, which is disposed between the fluid flow passageway and first compartment. The membrane is configured to affect flow through the fluid flow passageway by deflecting in response to pressure in the flow control chamber.

33 Claims, 3 Drawing Sheets

SEPARATION OF GAS AND LIQUID IN MEMBRANE VALVES

PRIORITY CLAIM

This application claims the benefit of priority of U.S. Provisional Patent Application Ser. No. 61/569,984 titled "SEPARATION OF GAS AND LIQUID IN MEMBRANE VALVES," filed on Dec. 13, 2011, whose inventor is Daryush Agahi, which is hereby incorporated by reference in its entirety as though fully and completely set forth herein.

BACKGROUND

The present disclosure relates generally to valves and associated systems and methods for use in ophthalmic treatments.

Glaucoma, a group of eye diseases affecting the retina and optic nerve, is one of the leading causes of blindness worldwide. Most forms of glaucoma result when the intraocular pressure (IOP) increases to pressures above normal for prolonged periods of time. IOP can increase due to high resistance to the drainage of the aqueous humor relative to its production. Left untreated, an elevated IOP causes irreversible damage to the optic nerve and retinal fibers resulting in a progressive, permanent loss of vision.

The eye's ciliary body continuously produces aqueous humor, the clear fluid that fills the anterior segment of the eye (the space between the cornea and lens). The aqueous humor flows out of the anterior chamber (the space between the cornea and iris) through the trabecular meshwork and the uveoscleral pathways, both of which contribute to the aqueous humor drainage system. The delicate balance between the production and drainage of aqueous humor determines the eye's IOP.

FIG. 1 is a diagram of the front portion of an eye that helps to explain the processes of glaucoma. In FIG. 1, representations of the lens 110, cornea 120, iris 130, ciliary body 140, trabecular meshwork 150, and Schlemm's canal 160 are pictured. Anatomically, the anterior segment of the eye includes the structures that cause elevated IOP which may lead to glaucoma. Aqueous humor fluid is produced by the ciliary body 140 that lies beneath the iris 130 and adjacent to the lens 110 in the anterior segment of the eye. This aqueous humor washes over the lens 110 and iris 130 and flows to the drainage system located in the angle of the anterior chamber. The angle of the anterior chamber, which extends circumferentially around the eye, contains structures that allow the aqueous humor to drain. The trabecular meshwork 150 is commonly implicated in glaucoma. The trabecular meshwork 150 extends circumferentially around the anterior chamber. The trabecular meshwork 150 seems to act as a filter, limiting the outflow of aqueous humor and providing a back pressure that directly relates to IOP. Schlemm's canal 160 is located beyond the trabecular meshwork 150. Schlemm's canal 160 is fluidically coupled to collector channels (not shown) allowing aqueous humor to flow out of the anterior chamber. The two arrows in the anterior segment of FIG. 1 show the flow of aqueous humor from the ciliary bodies 140, over the lens 110, over the iris 130, through the trabecular meshwork 150, and into Schlemm's canal 160 and its collector channels.

One method of treating glaucoma includes implanting a drainage device in a patient's eye. The drainage device allows fluid to flow from the interior chamber of the eye to a drainage site, relieving pressure in the eye and thus lowering IOP. In order to provide consistency and accuracy in fluid flow through the drainage device, it may be important to limit changes and degradation that may occur in the drainage device over time.

The system and methods disclosed herein overcome one or more of the deficiencies of the prior art.

SUMMARY

In one exemplary aspect, the present disclosure is directed to a drainage device for implantation in an eye of a patient to treat an ocular condition. The drainage device includes a housing, a flow control chamber within the housing, and a membrane. The housing includes an entrance port and an exit port connected by a fluid flow passageway. The flow control chamber includes a first compartment and a second compartment that is in fluid communication with the first compartment. Moreover, the first and second compartments are structurally arranged to limit contact of gas with the membrane, which is disposed between the fluid flow passageway and the first compartment. The membrane is configured to affect flow through the fluid flow passageway by deflecting in response to pressure in the flow control chamber.

In some instances, the drainage device further includes an actuator liquid and an electrolysis system configured to affect the pressure in the flow control chamber by generating bubbles by converting at least a portion of the actuator liquid to a gas.

In another exemplary aspect, the present disclosure is directed to an IOP control system for implantation in an eye of a patient. The IOP control system includes a drainage tube and an electrolysis-based membrane element. The drainage tube is configured to convey aqueous humor from an anterior chamber of the eye. The electrolysis-based membrane element is in fluid communication with the drainage tube, and includes a flow control chamber, a membrane, and a state-change generator. The flow control chamber includes a first compartment and a second compartment in fluid communication with the first compartment. Moreover, the first and second compartments are structurally arranged to limit contact of the gas with the membrane, which is disposed to define a portion of the first compartment. The membrane is configured to deflect in response to pressure changes within the flow control chamber. The state-change generator is disposed within the second compartment, and is configured to generate pressure within the flow control chamber by changing the state of an actuator liquid to a gas to effect a pressure change in the flow control chamber.

In yet another exemplary aspect, the present disclosure is directed to a method of regulating drainage from an anterior chamber of an eye with a membrane valve. The method includes directing fluid through a fluid flow passageway, which is formed within a housing including a flow control chamber and a flexible membrane. The membrane separates the fluid flow passageway from the flow control chamber, which includes a first compartment and a second compartment that are in fluid communication with each other and are cooperatively arranged to affect gas loss through the membrane. The method further includes modifying a size of the fluid flow passageway through the membrane valve in response to a flow control pressure acting on the membrane by deflecting the membrane to increase or decrease the size of the fluid flow passageway in the membrane valve.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
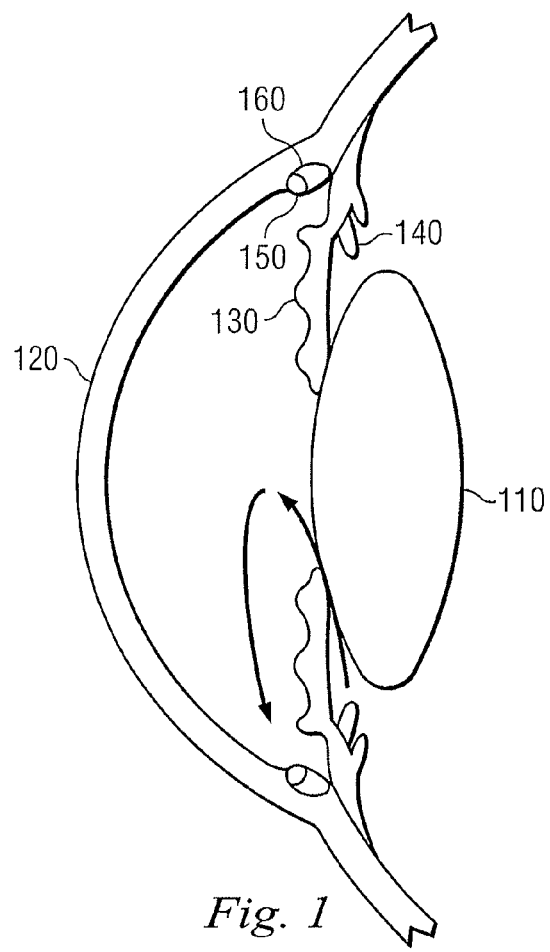
FIG. 1 is a diagram of the front portion of an eye.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For simplicity, in some instances the same reference numbers are used throughout the drawings to refer to the same or like parts.

The present disclosure relates generally to electrolysis-based membrane devices, and in particular to flow control chambers within electrolysis-based membrane devices. Electrolysis-based membrane devices utilize deflection of the membrane in response to pressure differentials across the membrane to regulate the flow through the drainage device. These pressure differentials may be obtained using phase-change processes that convert liquid to gas. However, gas molecules in membrane valves may diffuse through the membrane. As gas is lost through the membrane, a gas imbalance arises due to the unequal diffusion rates of various gases (e.g., hydrogen and oxygen, which have vastly different diffusion rates due to their molecular size difference). Such devices require a continuous supply of energy to generate sufficient gas through electrolysis to overcome both the loss of gas through the membrane and the gas recombination in order to maintain desired membrane deflection behavior.

Such electrolysis-based membrane devices include, by way of non-limiting example, valves and pumps. In some instances, embodiments of the present disclosure are configured to be part of an IOP control system. Those of skill in the art will realize that the flow control chambers disclosed herein may be utilized in similar applications requiring minimal or selective gas diffusion through a membrane.

The electrolysis-based membrane devices disclosed herein are shaped and configured to reduce the diffusion rate of gas through the membrane and provide for a controlled increase in the rate of gaseous recombination within the flow control chamber, thereby increasing the longevity, reliability, and speed of valve actuation. In particular, each of the electrolysis-based membrane devices of the present disclosure include a flow control chamber shaped and configured to separate the gases produced within the flow control chamber from the membrane. In some embodiments, the flow control chamber is partially divided into two compartments that are connected by a third compartment or channel adjacent a flexible membrane. By allowing for the segregation of different gases, this configuration permits a controlled increase in the rate of gaseous recombination, thereby allowing for rapid device actuation. In other embodiments, the flow control chamber comprises a first compartment separated from the flexible membrane by a second compartment or channel. By separating the gases from the membrane, the flow control chambers disclosed herein reduce the inadvertent escape of gas through the membrane that may arise in IOP control systems utilizing electrolysis-based devices with single-compartment flow control chambers. The reduction in the escape of gas through the membrane provides an increase in the longevity and the reliability of device actuation by aiding the gas molecular ratio within the flow control chamber to stay in balance. Thus, the flow control chambers disclosed herein may optimize the performance of electrolysis-based devices utilizing membrane actuators within an IOP control system.

Figure 2:
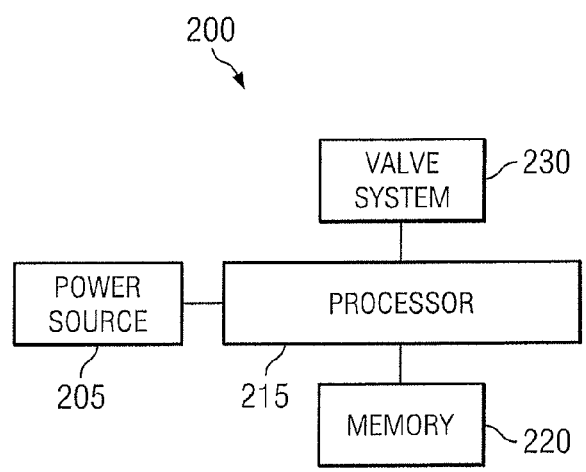
FIG. 2 is a block diagram of an exemplary IOP control system according to the principles of the present disclosure.

FIG. 2 is a block diagram of an exemplary IOP control system 200 implantable in an eye of a patient for the treatment of glaucoma or other conditions. The IOP control system 200 is configured in a manner that provides IOP pressure control, but also regulates and controls bleb pressures, reducing complications arising from surgical implant glaucoma treatments. In FIG. 2, the IOP control system 200 includes a power source 205, a processor 215, a memory 220, and a valve system 230.

The power source 205, which provides power to the system 200, is typically a rechargeable battery, such as a lithium ion or lithium polymer battery, although other types of batteries may be employed. The power source can be recharged via inductive coupling such as an RFID link or other type of magnetic coupling.

The processor 215 is typically an integrated circuit with power, input, and output pins capable of performing logic functions. In various embodiments, the processor 215 may be a targeted device controller or a microprocessor configured to control more than one component of the device.

The memory 220, which is typically a semiconductor memory such as RAM, FRAM, or flash memory, interfaces with the processor 215. As such, the processor 215 can write to and read from the memory 220, and perform other common functions associated with managing semiconductor memory. In this manner, a series of IOP readings can be stored in the memory 220.

The IOP control system 200 is described below with reference to FIG. 3, and the valve system 230 is described below with reference to FIGS. 4-7.

Figure 3:
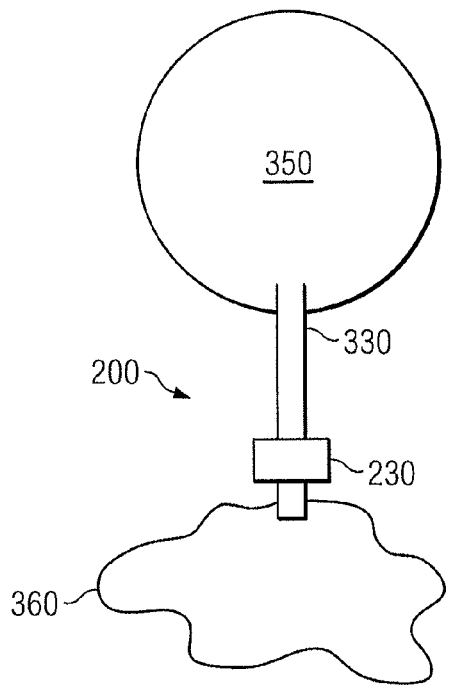
FIG. 3 is a schematic diagram of an exemplary IOP control system according to the principles of the present disclosure.

FIG. 3 is a diagram of the exemplary IOP control system 200, including a drainage tube 330 and the valve system 230. The drainage tube 330 drains aqueous humor from the anterior chamber 350 of the eye to a drainage site 360. The valve system 230 controls the flow of aqueous humor through the tube 330.

The valve system 230 may be controlled by microprocessor 215 based on input data received from, by way of non-limiting example, sensors or data or a programmed treatment plan. A desired pressure differential (that corresponds to a flow rate) can be maintained by controlling the operation of the valve system 230. Likewise, various intraocular pressure parameters, such as, by way of non-limiting example, the desired IOP, the IOP change rate, and/or the bleb pressure may be controlled by controlling the operation of valve system 230.

Figure 4:
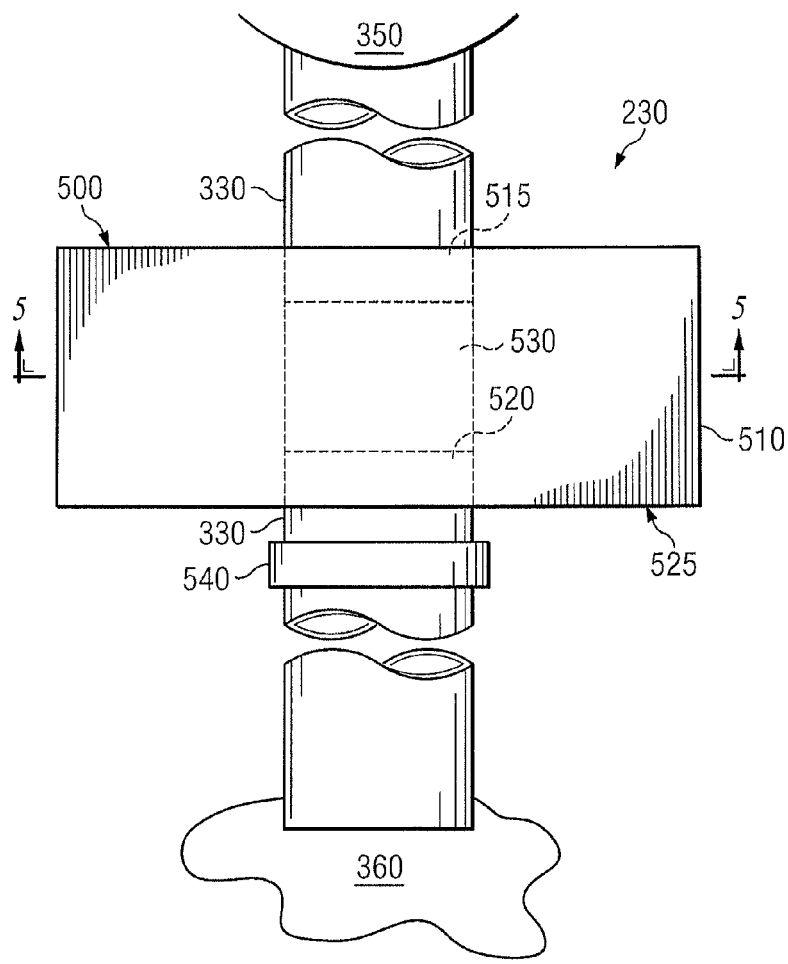
FIG. 4 is a schematic illustration of a top view of an exemplary IOP control system including an exemplary membrane valve in accordance with one embodiment of the present disclosure.

FIG. 4 shows a top view of an exemplary electrolysis-based membrane valve 500 within the valve system 230. The valve system 230 is disposed along, and may form a part of, the drainage tube 330 between the tube end in the anterior chamber 350 and the drainage site 360.

In the pictured embodiment, the valve system 230 is configured to control the flow of drainage fluid from the anterior chamber 350 through the drainage tube 330 and the valve 500 to the drainage site 360, and thereby control pressure in the eye, including the IOP. For example, when IOP is high, the valve system 230 may operate to permit increased flow through the drainage tube, and when IOP is low, the valve system 230 may operate to decrease the flow through the drainage tube. In addition, the valve system 230 is configured to adjust the flow of drainage fluid to the bleb, and thereby control the bleb pressure to maintain a desired fluid flow to the bleb. This may decrease fibrosis and increase absorption efficiency. To accomplish this, the valve system 230 is responsive to signals sent as instructions from the processor 215.

In the example in FIG. 4, the electrolysis-based membrane valve 500 includes a housing 510 with an entrance port 515, an exit port 520, and a flow control system 525 inside the housing. The housing 510 may be constructed of any suitable biocompatible material, provided the material is able to maintain constructional integrity during pressure changes. The flow control system 525 includes a fluid flow passageway 530 extending between the entrance port 515 and the exit port 520 and a multi-compartment flow control chamber 535 (shown in FIG. 5).

The entrance port 515 connects to the drainage tube 330 and is configured to receive aqueous humor flowing from the drainage tube 330 into the valve system 230. The exit port 520 permits fluid to exit the housing 510 for further regulation within other structures 540 in the valve system 230 or for release at the drainage site 360. Fluid flows from the drainage tube 330 into the entrance port 515, through the fluid flow passageway 530, out the exit port 520, and through any other structures 540, such as, by way of non-limiting example, redundant or special purpose valves and/or pumps, before exiting the valve system 230 to enter the drainage site 360. Various embodiments of the valve system 230 may include any number of the structures 540, including those having features similar to the flow control system 525. Some embodiments lack the structures 540.

Figure 5:
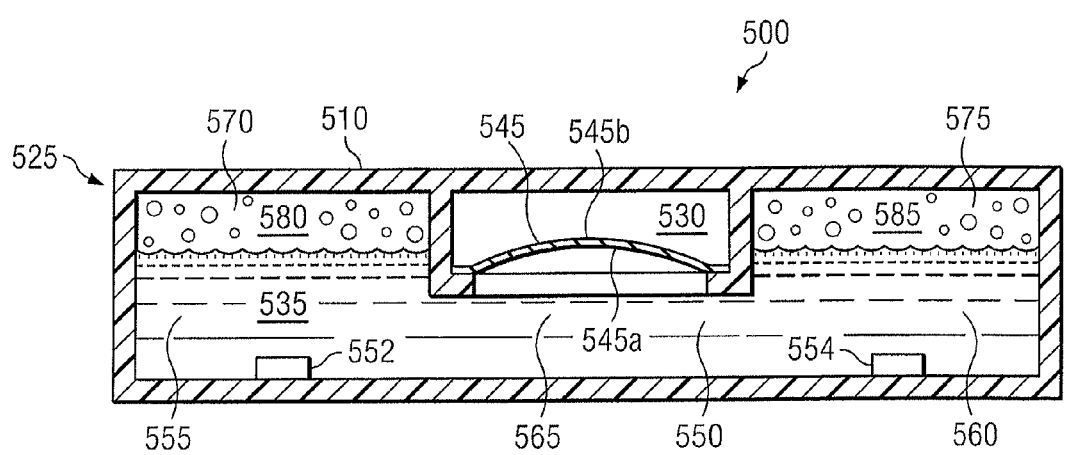
FIG. 5 is an illustration of a cross-sectional view of the exemplary membrane valve shown in FIG. 4 in accordance with one embodiment of the present disclosure.

FIG. 5 illustrates a cross-sectional view along lines 5-5 of the electrolysis-based membrane valve 500 shown in FIG. 4. In addition to the fluid flow passageway 530, the valve 500 includes the multi-compartment flow control chamber 535, a membrane 545 anchored to the housing 510, actuator liquid 550 within the flow control chamber 535, and a state-change generator or electrodes 552, 554 arranged to cooperate with the actuator liquid 550. In alternative embodiments, a plurality of membranes using separate fluid flow passageways is contemplated for use in the valve 500.

The fluid flow passageway 530 is separated from the multi-compartment flow control chamber 535 by the membrane 545. The membrane 545 comprises a flexible, deformable, liquid-tight membrane or diaphragm that provides valve functionality by deflecting in response to pressure differentials across its two opposing sides. The membrane 545 is anchored to the housing 510 at its periphery to form one side of the fluid flow passageway 530. The membrane is securely held in place within the housing 510 so that it will not be displaced by the force of the fluid flowing through the valve 500. The membrane 545 may be formed of a biocompatible elastomeric material such as, by way of non-limiting example, Parylene, a silicone, silicone nitride, silicone elastomeric, and polyimide.

The membrane 545 includes two generally parallel surfaces, a surface 545a and an opposite surface 545b. The surface 545a faces a compartment 565 of the flow control chamber 535, and consequently conveys the flow control pressure within the flow control chamber. The surface 545b faces the fluid flow passageway 530, and consequently conveys the pressure within the fluid flow passageway. In some embodiments, the surface 545b faces the entrance port 515, and consequently conveys the pressure of the anterior chamber. In some embodiments, the membrane 545 and its surface 545b selectively seal the fluid flow passageway 530 and thereby reduce or eliminate flow through the valve 500 when the pressure against the surface 545a sufficiently outweighs the pressure against the surface 545b.

The valve 500 is configured as a throttle valve that can completely or partially block the flow of aqueous humor by deflecting the membrane 545 into the fluid flow passageway 530. The housing 510 is configured to connect with the drainage tube 330 such that deflection of the membrane 545 at least partially opens and closes the fluid flow passageway 530 to allow the flow of aqueous humor in through the entrance port and out the exit port 520. As described above, the position of the membrane 545 determines whether the valve 500 is in an open or closed condition.

The membrane 545 forms a sealed barrier between the fluid flow passageway 530 and the flow control chamber 535, effectively separating between the pressure in the passageway 530 and the pressure within the flow control chamber 535. Accordingly, as the pressure increases against one side of the membrane 545, the membrane 545 deflects in the direction away from the higher pressure.

The membrane 545 deflects in response to pressure differences between the entrance port 515 and the flow control chamber 535 to at least partially open or close the valve 500 by changing the dimensions of the fluid flow passageway 535. The size of the fluid flow passageway 530 affects the rate of flow.

When the pressure differential across the membrane causes the membrane to deflect away from the flow control chamber 535, the cross-sectional area of the fluid flow passageway 530 is reduced, thereby reducing or eliminating the flow of aqueous humor through the valve 500. Conversely, when the pressure differential across the membrane causes the membrane to deflect toward the flow control chamber 535, the cross-sectional area of the fluid slow passageway 530 is increased, thereby augmenting the flow of aqueous humor through the valve 500.

In the example shown, the flow control chamber 535 comprises a multi-compartment structure including a compartment 555 and a compartment 560 connected by the compartment 565. The flow control chamber 535 is shaped to have rigid walls on all but one side, which is formed by the flexible membrane 545. In the pictured embodiment, the membrane 545 is adjacent to and forms a ceiling of the compartment 565. As mentioned above, the flow control chamber 535 is sealed closed and separated from the fluid flow passageway 530 by the membrane 545. Accordingly, as volume increases within the chamber 535, the concomitant pressure increase within the chamber 535 acts to displace the membrane 545 in only one direction (i.e., away from the compartment 565 into the fluid flow passageway 530).

The actuator liquid 550 is contained in the flow control chamber 535 and includes, in some embodiments, water. Some embodiments include a water-based electrolyte solution, such as a saline composition formed of sodium chloride in the water. Other liquids are also contemplated for use as the actuator liquid, including reactive materials such as, by way of non-limiting example, sulfuric acid.

The electrodes 552, 554 are disposed within the actuator liquid 550 in a manner permitting at least a portion of the ions and electrolytes in the actuator liquid 550 to phase change from liquid to gas, forming gas-filled bubbles within the flow control chamber 535 through electrolysis. As the bubbles form, the pressure in the chamber 535 increases, thereby increasing the overall pressure. This increased pressure acts on the membrane 545 to cause its displacement into the fluid flow passageway 530. The electrodes 552, 554 are in electrical communication with the power source 205, which is controlled by the processor 215. Through the electrolysis, water in the actuator liquid 550 may result in hydrogen and oxygen molecules. In some embodiments, the electrodes 552, 554 may be interdigitated for efficient and effective electrolysis.

In the pictured embodiment, the electrode 552 is positioned within the compartment 555, and the electrode 554 is positioned within the compartment 560. In operation, when a voltage is applied to the two electrodes 552, 554, the multi-compartment structure of the flow control chamber 535 allows a first gas 570 to form in one compartment and a second gas 575 to form in the other compartment. For example, in the illustrated embodiment, the voltage polarity may be applied such that the electrode 552 is the anode and the electrode 554 is the cathode, causing hydrogen molecules to form in compartment 555 and oxygen molecules to form within the compartment 560. In particular, when the voltage polarity is switched, the electrode 552 becomes the cathode and the electrode 554 becomes the anode, causing oxygen molecules to form in the compartment 555 and hydrogen molecules to form within the compartment 560. Note that the number and arrangement of the electrodes may be changed to achieve a desired level and type of gas production.

In use, the IOP control system 200 is implanted in an eye in a conventional manner. The processor 215 of the IOP control system adjusts the flow through the valve system 230 based on measured pressure values or derivatives from pressure sensors, based in pre-stored treatment plans, or based on other factors. If the pressures are not within desired ranges, the IOP control system 200 may adjust the valve system 230 to increase or decrease drainage flow through the drainage tube 330 to maintain the IOP as desired. To do this, the processor 215 operates the valve system 230 with the power source 205 to activate or deactivate the electrodes 552, 554 in the membrane valve 500 and/or the other structures 540. The electrodes 552, 554 act within the actuator liquid 550 to change at least a portion of the liquid to a gaseous state, thereby increasing the pressure within the flow control chamber 535.

In particular, as the electrodes 552, 554 generate bubbles of gas in the actuator liquid 550 through electrolysis, the pressure increases within the chamber of the flow control chamber 535. As the liquid state of the actuator liquid 550 partially changes to a gaseous state, and the gases 570, 575 are formed, the increasing pressure in the flow control chamber 535 acts against the flexible membrane 545 to displace it and increase the overall volume of the chamber. Thus, as the pressure increases, the membrane 545 expands into the fluid flow passageway 530, decreasing the cross-sectional area of the fluid flow passageway 530, thereby restricting some fluid flow from the drainage tube 330. In a similar, but opposite manner, when the gases 570, 575 recombine and the solution in the flow control chamber 535 returns to its more fluid state, the volume in the flow control chamber 535 decreases, permitting the membrane 545 to move further out of the fluid flow passageway 530, thereby permitting an increased level of fluid flow from the drainage tube 330 through the passageway 530.

The gases 570, 575 separate from the actuator liquid 550 to create gaseous areas 580, 585, respectively, within the volumes of the compartments 555, 560, respectively. Areas 580, 585 are separated from and are not in contact with the membrane 545 or each other. Thus, the gases 570, 575 are substantially isolated from the membrane 545 and are segregated from each other. The multi-compartment structure of the flow control chamber 535 hinders or prevents the gases 570, 575 from directly contacting the membrane surface 545a. Therefore, the gases are unable to permeate through the membrane 545 into the drainage flow. Accordingly, the loss of gases from the flow control chamber 535 is reduced or eliminated. Here, the membrane is maintained in contact with the liquid, but not the gases because the membrane is maintained at an elevation lower than that of the gases. That is, because the membrane 545 is maintained below the liquid level of the compartments 555, 560, the membrane 545 responds as though it is submerged in the liquid. In addition, while the valve's orientation changes with the patient's physical position (e.g., sitting up, lying down, etc.), the multi-chamber here permits any gases that pass past the membrane to be maintained substantially in areas of the flow control chamber 535 out of contact with the membrane 545.

This separation of the gases 570, 575 from the membrane 545 reduces the rate of diffusion of the gases out of the flow control chamber 535 through the membrane 545, thereby increasing valve reliability by aiding the gas molecular ratio to stay in balance (e.g., one oxygen per two hydrogens) within the chamber 535. By aiding the gas molecular ratio to stay in balance within the flow control chamber 535, the multi-compartment design of the flow chamber 535 reduces the overall amount of energy required to power the valve 500. It is worth noting that the ratio of liquid to gas in FIG. 5 is not to scale, and the large gas volume is shown only for ease of explanation.

Moreover, in this example where the anode electrode and the cathode electrode are in different compartments, the corresponding hydrogen and oxygen molecules accumulate in the respective areas 580, 585. The segregation of the gases 570, 575 from each other within the separate areas 580, 585 slows the recombination of the hydrogen and oxygen molecules, once the molecules are phase-changed from liquid to gas. The segregation of the gases 570, 575 prolongs the state change from gas back to liquid. This likewise prolongs periods of steady pressure with minimal energy consumption. As described above, due to the state changes, the membrane 545 flexes or deflects to increase or decrease the cross-sectional area of the fluid flow passageway 530 to affect flow resistance, and ultimately control pressure by regulating flow. Accordingly, at least a portion of the actuator liquid 550 may be held in a gaseous state for a sufficient length of time to provide regulatory control of the aqueous humor through the fluid flow passageway 530 in the valve 500 without a continuous application of energy to the system, thereby reducing the amount of energy required.

In addition, by compartmentalizing the gases 570, 575 away from each other, the multi-compartment design of the flow control chamber 535 facilitates the rapid and controlled generation of the second gas 575 within an area containing the first gas 570, and visa-versa, with a switch in voltage polarity. In particular, when the voltage polarity is switched, the electrode 552 becomes the cathode and the electrode 554 becomes the anode, causing the second gas 570 to form in the compartment 555 and the first gas 575 to form within the compartment 560. Thus, in this example, oxygen may form in the area 585 and hydrogen may form in the area 580. This ability to rapidly switch the type of molecule produced within each compartment increases the recombination rate of the gaseous molecules within each compartment, thereby rapidly decreasing the pressure within the flow control chamber 535 and allowing the membrane 545 to quickly shift out of the fluid flow passageway 530, thereby facilitating rapid valve actuation. Some embodiments include a catalyst within the flow control chamber 535 to help increase the rate of recombination.

Figure 6:
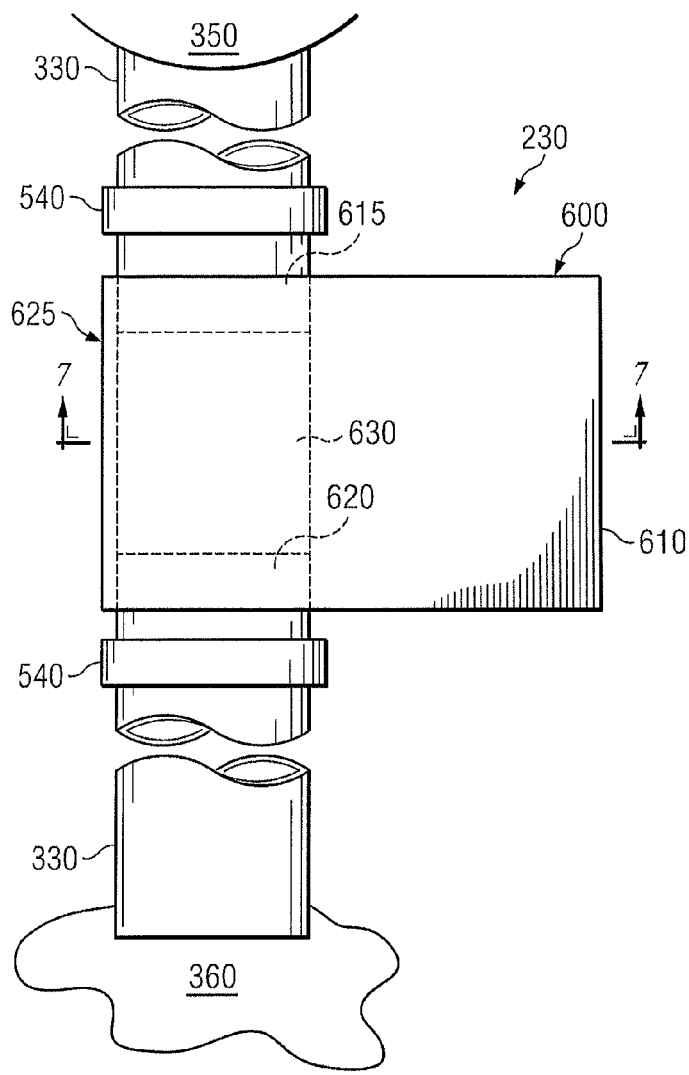
FIG. 6 is an illustration of a top view of an exemplary IOP control system including an exemplary membrane pump in accordance with one embodiment of the present disclosure.

FIG. 6 shows a top view of an exemplary electrolysis-based membrane pump 600 that may form part of the valve system 230 in addition to or in place of the valve 500. As described above, the valve system 230 is disposed along, and may form a part of, the drainage tube 330 between the tube end in the anterior chamber 350 and the drainage site 360.

In the example in FIG. 6, the electrolysis-based membrane pump 600 includes a housing 610 with an entrance port 615, an exit port 620, and a flow control system 625 inside the housing. The housing 610, the entrance port 615, the exit port 620, and the flow control system 625 are similar to the housing 510, the entrance port 515, the exit port 520, and the flow control system 525, respectively, except for the differences noted herein. The flow control system 625 includes a fluid flow passageway 630 extending between the entrance port 615 and the exit port 620 and a multi-compartment flow control chamber 635 (shown in FIG. 7).

The entrance port 615 connects to the drainage tube 330 and is configured to receive aqueous humor flowing from the drainage tube 330 (and/or other structures 540) into the valve system 230. The exit port 620 permits fluid to exit the housing 610 for further regulation within other structures 540 in the valve system 230 or for release at the drainage site 360. Fluid flows from the drainage tube 330 (and/or other structures 540) into the entrance port 615, is pumped through the fluid flow passageway 630, flows out the exit port 620, and flows through any other structures 540, such as, by way of non-limiting example, valves and/or pumps, before exiting the valve system 230 to enter the drainage site 360. Various embodiments of the valve system 230 may include any number of the structures 540. Some embodiments lack the structures 540.

Figure 7:
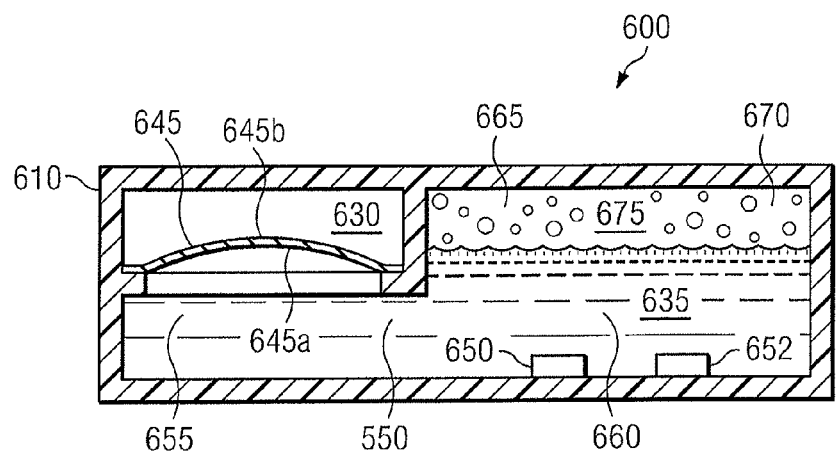
FIG. 7 is an illustration of a cross-sectional view of the exemplary membrane pump shown in FIG. 6 in accordance with one embodiment of the present disclosure.

FIG. 7 illustrates a cross-sectional view along lines 7-7 of the electrolysis-based membrane pump 600 shown in FIG. 4 in accordance with one embodiment of the present disclosure. In addition to the fluid flow passageway 630 and the multi-compartment flow control chamber 635, the pump 600 includes a membrane 645 anchored to the housing 610, the actuator liquid 550 within the flow control chamber 635, and electrodes 650, 652 arranged to cooperate with the actuator liquid 550. In alternative embodiments, a plurality of membranes using separate fluid flow passageways is contemplated for use in the pump 600.

The fluid flow passageway 630 is separated from the multi-compartment flow control chamber 635 by the membrane 645. The membrane 645 comprises a flexible, deformable, liquid-tight membrane or diaphragm that is similar to the membrane 545 except for the differences described herein. The membrane 645 includes two generally parallel surfaces, a surface 645a, which conveys the flow control chamber pressure within the flow control chamber 635, and an opposite surface 645b, which conveys the pressure within the fluid flow passageway 630. The membrane 645 and the surface 645b of the membrane 645 selectively seal the fluid flow passageway 630 and thereby reduce or eliminate flow through the pump 600 when the pressure against the surface 645a sufficiently outweighs the pressure against the surface 645b.

The pump 600 is configured to completely or partially block the flow of aqueous humor by deflecting the membrane 645 into the fluid flow passageway 630. The housing 610 is configured to connect with the drainage tube 330 such that deflection of the membrane 645 at least partially opens and closes the fluid flow passageway 630 to allow flow of aqueous humor in through the entrance port 615 and out through the exit port 620.

The membrane 645 forms a sealed barrier between the fluid flow passageway 630 and the flow control chamber 635, effectively separating the pressure within the drainage tube 330 proximal to the pump 600 and the pressure within the flow control chamber 635. Accordingly, as the pressure increases against one side of the membrane 645, the pressure increase acts to deflect the membrane 645 in the direction away from the higher pressure as described with reference to membrane 545 above.

The flow control chamber 635 is similar to the flow control chamber 545 except for the differences noted herein. In the example shown in FIG. 7, the flow control chamber 635 comprises a multi-compartment structure including a compartment 655 and a compartment 660. The flow control chamber 635 is shaped to have rigid walls on all but one side, which is formed by the flexible membrane 645. In the pictured embodiment, the membrane 645 is adjacent to and forms a ceiling of the compartment 655. As mentioned above, the flow control chamber 635 is sealed closed and separated from the fluid flow passageway 630 by the membrane 645. Accordingly, as pressure increases within the flow control chamber 635, the membrane 645 displaces in a direction away from the area conveying greater pressure (e.g., away from the flow control chamber 635 into the fluid flow passageway 630).

The electrodes 650, 652 are similar to the electrodes 552, 554, respectively, except for the differences noted herein. In the pictured embodiment, the electrodes 650, 652 are both positioned within the same compartment 660.

The gases 665, 670 represent the gases created by each of the electrodes, and separate from the actuator liquid 550 to create area 675 within the compartment 660. The area 675 is separated away from and is not in contact with the membrane 645. Thus, the gases 665, 670 are substantially isolated from the membrane 645. The multi-compartment structure of the flow control chamber 635 hinders or prevents the gases 665, 670 from directly contacting the membrane surface 645a, reducing the rate of diffusion of the gases out of the flow control chamber 635 through the membrane 645 as described above with reference to valve 500.

The generation of gases 665, 670 within the same compartment 660 facilitates the rapid recombination of gases. In particular, the gases 665, 670 occupy the same area 675 and can recombine quickly by virtue of proximity. This rapid recombination rate facilitates the rapid decrease of pressure within the flow control chamber 635 and facilitates rapid actuation of the pump 600.

It is worth noting that for biocompatibility, the devices disclosed herein may be coated or encapsulated in a material such as polypropylene, silicon, parylene, or other materials.

The systems and methods described herein achieve IOP control with very low power and with a very small device. The electrolysis-based devices, systems, and methods disclosed herein accomplish this using electrolysis and a multi-compartment flow control chamber to affect drainage flow. The embodiments of the present disclosure also take into account gas permeability and gas recombination in regulating drainage flow. In particular, these embodiments include a multi-compartment flow control chamber capable of slowing the escape of gas and of being controlled in a way that increases the rate of gaseous recombination in an electrolysis-based membrane device. The multi-compartment flow control chamber allows for the reduction in gas permeability within the valve, thereby increasing the longevity and reliability of valve actuation by aiding the gas molecular ratio to stay in balance. In addition, an embodiment of the multi-compartment flow control chamber described herein may be controlled to increase the recombination rate of gas molecules within the chamber to facilitate rapid valve actuation. By preventing inadvertent gas imbalance and allowing for rapid valve actuation, the multi-compartment flow control chamber reduces the need for constant energy to power the device. Thus, the devices, systems, and methods disclosed herein may reduce the diffusion rate of gas through the membrane and increase the rate of gaseous recombination within the flow control chamber, thereby increasing the longevity, reliability, and speed of valve actuation.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

I claim:

1. A drainage device for implantation in an eye of a patient to treat an ocular condition, comprising:
   a housing including an entrance port and an exit port connected by a fluid flow passageway;
   a flow control chamber within the housing including a first compartment and including a second compartment open to the first compartment;
   a membrane disposed between the fluid flow passageway and the first compartment, the membrane configured to affect flow through the fluid flow passageway by deflecting in response to pressure in the flow control chamber, wherein the first and second compartments are structurally arranged to limit contact of gas with the membrane; and
   electrodes disposed within the second compartment to generate a gas from an actuator liquid present in the flow control chamber thereby effecting a pressure change in the flow control chamber, wherein the first and second compartments are structurally arranged so that the membrane is maintained at an elevation lower than that of the gas within the flow control chamber to limit contact of the gas with the membrane.

2. The drainage device of claim 1, wherein the flow control chamber includes an actuator liquid and an electrolysis system configured to affect the flow control chamber pressure by generating bubbles by converting at least a portion of the actuator liquid to a gas.

3. The drainage device of claim 2, wherein the electrolysis system includes a first electrode and a second electrode, and wherein one of the first and second electrodes is an anode and the other of the first and second electrodes is a cathode.

4. The drainage device of claim 3, wherein the flow control chamber includes a third compartment, and wherein the first compartment connects the second compartment to the third compartment.

5. The drainage device of claim 4, wherein the first electrode is disposed adjacent the actuator liquid in the second compartment, and the second electrode is disposed adjacent the actuator liquid in the third compartment.

6. The drainage device of claim 5, wherein the first electrode is located to generate a first gas within the second compartment and the second electrode is located to generate a second gas within the third compartment.

7. The drainage device of claim 6, wherein the compartments are shaped and configured to segregate the first gas from the second gas.

8. The drainage device of claim 6, wherein the first, second, and third compartments are shaped and configured to substantially segregate the first gas and the second gas from the membrane.

9. The drainage device of claim 6, wherein the flow control chamber includes at least one catalyst to increase a recombination rate of the first gas and the second gas.

10. The drainage device of claim 3, wherein the first electrode and the second electrode are disposed adjacent the actuator liquid in the second compartment.

11. The drainage device of claim 10, wherein a first gas and a second gas are formed within the second compartment.

12. The drainage device of claim 1, wherein the first and second compartments are shaped and configured to segregate a first gas and a second gas from the membrane.

13. The drainage device of claim 1, wherein the flow control chamber includes at least one catalyst to increase a recombination rate of a first gas and a second gas within the flow control chamber.

14. The drainage device of claim 1, wherein the TOP control device comprises a valve.

15. The drainage device of claim 1, wherein the TOP control device comprises a pump.

16. An IOP control system for implantation in an eye of a patient, comprising:
   a drainage tube configured to convey aqueous humor from an anterior chamber of the eye; and
   an electrolysis-based membrane element forming a fluid flow passageway disposed along the drainage tube, the element comprising:
      a flow control chamber including a first compartment and including a second compartment that is open to the first compartment;
      a membrane disposed to define a portion of the first compartment and a portion of the fluid flow passageway, the membrane being configured to deflect in response to pressure changes within the flow control chamber; and
      a state-change generator disposed within the second compartment and configured to generate pressure within the flow control chamber by changing the state of a portion of an actuator liquid to a gas to effect a pressure change in the flow control chamber, wherein the first and second compartments are structurally arranged so that the membrane is maintained at an elevation lower than that of the gas within the flow control chamber to limit contact of the gas with the membrane.

17. The IOP control system of claim 16, wherein the state-change generator includes a first electrode and a second electrode that generate bubbles by converting at least a portion of the actuator liquid to a gas, and wherein one of the first and second electrodes is an anode and the other of the first and second electrodes is a cathode.

18. The IOP control system of claim 17, wherein the flow control chamber includes a third compartment in fluid communication with the first compartment and the second compartment.

19. The IOP control system of claim 18, wherein the first electrode is disposed adjacent the actuator liquid in the second compartment, and the second electrode is disposed adjacent the actuator liquid in the third compartment.

20. The IOP control system of claim 19, wherein the first electrode is disposed to form a first gas within the second compartment and the second electrode is disposed to form a second gas within the third compartment.

21. The IOP control system of claim 20, wherein the compartments are shaped and configured to substantially segregate the first gas from the second gas.

22. The IOP control system of claim 20, wherein the compartments are shaped and configured to substantially segregate the first gas and the second gas from the membrane.

23. The IOP control system of claim 17, wherein the first electrode and the second electrode are disposed adjacent the actuator liquid in the second compartment, and wherein a first gas and a second gas are formed within the second compartment.

24. The IOP control system of claim 23, wherein the first and second compartments are shaped and configured to segregate the first gas and the second gas from the membrane.

25. The IOP control system of claim 23, further comprising a pump.

26. An IOP control system for implantation in an eye of a patient, comprising: a flow control chamber having a first side and an opposing second side and having a first compartment and a second compartment defined therein, the first and second compartments being open to each other; a membrane forming a ceiling of the first compartment, the membrane being configured to deflect away from the opposing second side of the flow control chamber and into a fluid flow passageway in response to a pressure increase within the flow control chamber; a state-change generator disposed within the second compartment and on the opposing second side, the state-change generator being configured to cause the pressure increase within the flow control chamber by changing a portion of an actuator liquid contained within the first and second compartments to a gas, and wherein the first and second compartments are structurally arranged so that the membrane is maintained at an elevation lower than that of the gas so that the gas rises toward the first side of the flow control chamber such that the gas is captured within the second compartment; and a drainage tube in fluid communication with the membrane.

27. The IOP control system of claim 26, wherein the ceiling of the first compartment is closer to the opposing second side than a gaseous area of the second compartment that contains the gas.

28. The IOP control system of claim 26, wherein deflection of the membrane away from the opposing second side of the flow control chamber causes a decrease in flow through the drainage tube.

29. The IOP control system of claim 27, wherein the gas is captured within the second compartment in a gaseous area contacting the first side of the flow control chamber.

30. The IOP control system of claim 26, wherein the flow control chamber includes a third compartment in fluid communication with the first compartment and the second compartment such that the actuator liquid flows freely among the first, second, and third compartments.

31. The IOP control system of claim 30, wherein a first electrode of the state-change generator is disposed in the second compartment and a second electrode is disposed in the third compartment.

32. The IOP control system of claim 31, wherein the first electrode is configured to form a first gas within the second compartment and the second electrode is configured to form a second gas within the third compartment, the first gas being different from the second gas.

33. The IOP control system of claim 31, wherein the compartments are shaped and configured to prevent the first gas and the second gas from contacting the membrane.

* * * * *